United States Patent [19]

Chow et al.

[11] Patent Number: 4,633,861
[45] Date of Patent: Jan. 6, 1987

[54] SURGICAL STAPLING INSTRUMENT WITH JAW CLAMPING MECHANISM

[75] Inventors: Hector Chow, Cincinnati; Hugh Melling, West Chester; Denise S. Schieltz, Cincinnati, all of Ohio

[73] Assignee: Senmed, Inc., Cincinnati, Ohio

[21] Appl. No.: 662,622

[22] Filed: Oct. 19, 1984

[51] Int. Cl.[4] .................. A61B 17/10; A61B 17/32
[52] U.S. Cl. ....................... 128/305; 128/334 R; 227/19; 227/153; 227/DIG. 1
[58] Field of Search ............ 128/334 R, 305; 227/19, 227/DIG. 1, 135, 152, 76, 153

[56] References Cited

U.S. PATENT DOCUMENTS

| | | | |
|---|---|---|---|
| D. 272,851 | 2/1984 | Green et al. | D24/26 |
| D. 272,852 | 2/1984 | Green et al. | D24/26 |
| 960,300 | 6/1910 | Fischer | 227/152 |
| 2,344,071 | 3/1944 | Wilson et al. | 227/19 |
| 3,017,637 | 1/1962 | Sampson | 227/19 X |
| 3,078,465 | 2/1963 | Bobrov | 128/334 R |
| 3,079,606 | 3/1963 | Bobrov | 227/76 |
| 3,315,863 | 4/1967 | O'Dea | 227/19 |
| 3,317,105 | 5/1967 | Astafjev et al. | 128/334 R X |
| 3,490,675 | 1/1970 | Green et al. | 227/19 |
| 3,499,591 | 3/1970 | Green | 227/76 |
| 3,551,987 | 1/1971 | Wilkinson | 128/334 R |
| 4,111,206 | 9/1978 | Vishnevsky et al. | 128/334 R X |
| 4,241,861 | 12/1980 | Fleischer | 227/135 |
| 4,244,372 | 1/1981 | Kapitanov et al. | 227/DIG. 1 X |
| 4,290,542 | 9/1981 | Fedotov et al. | 227/DIG. 1 X |
| 4,328,805 | 5/1982 | Akopov et al. | 128/334 R |
| 4,429,695 | 2/1984 | Green | 128/334 R X |
| 4,520,817 | 6/1985 | Green | 128/305 |

FOREIGN PATENT DOCUMENTS 1213583 3/1983 Australia .
599799 3/1978 U.S.S.R. ............ 227/DIG. 1

Primary Examiner—Paul E. Shapiro
Attorney, Agent, or Firm—Charles P. Boukus, Jr.; Jerrold J. Litzinger

[57] ABSTRACT

A surgical stapling instrument suitable for performing a gastrointestinal anastomosis is provided. The stapling instrument incorporates a jaw clamping mechanism which applies clamping forces to its jaw members to resist the forces exerted on the anvil and staple cartridge carrying portions of the jaw members when the staples are formed. Preferably, the stapling instrument includes a pair of elongate jaw members, one of which supports a staple cartridge adapted to receive at least two laterally spaced longitudinal rows of staples, and the other provided with an anvil adapted to form the staples. A pusher bar and knife blade assembly is slidable longitudinally relative to the jaw members to sequentially drive the staples from the cartridge and form the staples against the anvil to produce a pair of laterally spaced rows in the tissue. The pusher bar and knife blade assembly includes a knife blade for cutting the tissue along a line between the longitudinal staple rows. A latching mechanism is provided for latching the jaw members together at an intermediate position therealong adjacent to the staple cartridge and the anvil. In addition, a cam mechanism is provided for urging the jaw members apart at a position remote from the latching mechanism to resist the forces exerted on the staple cartridge and anvil when the pusher bar and knife blade assembly is actuated to staple and cut the tissue gripped between the jaw members.

22 Claims, 21 Drawing Figures

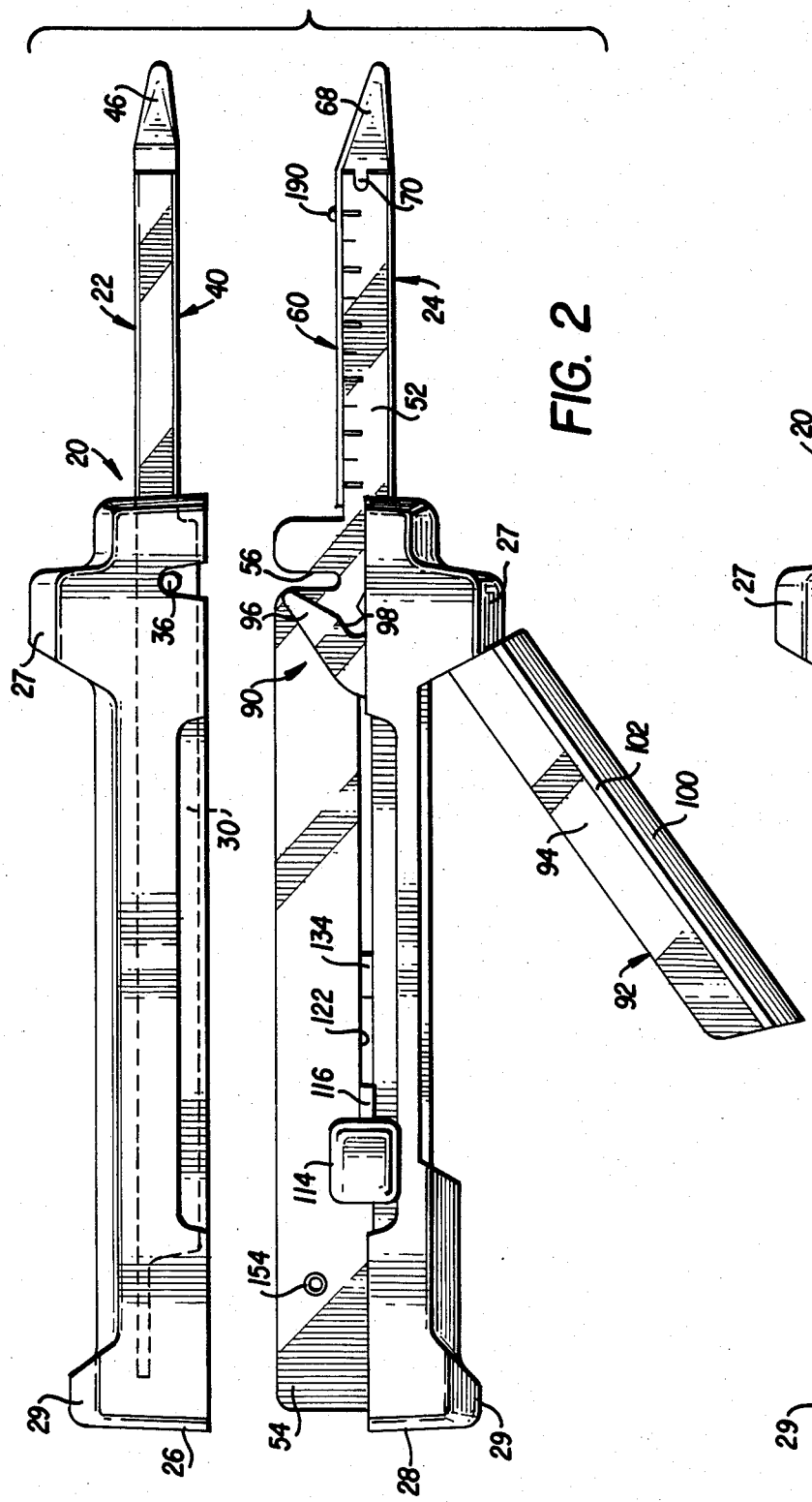
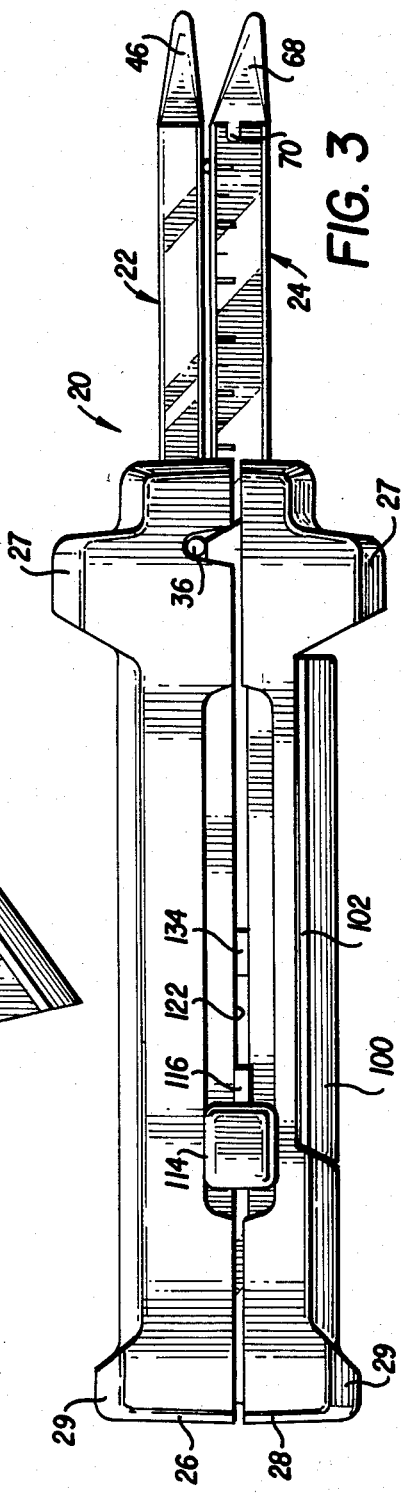
FIG. 2
FIG. 3

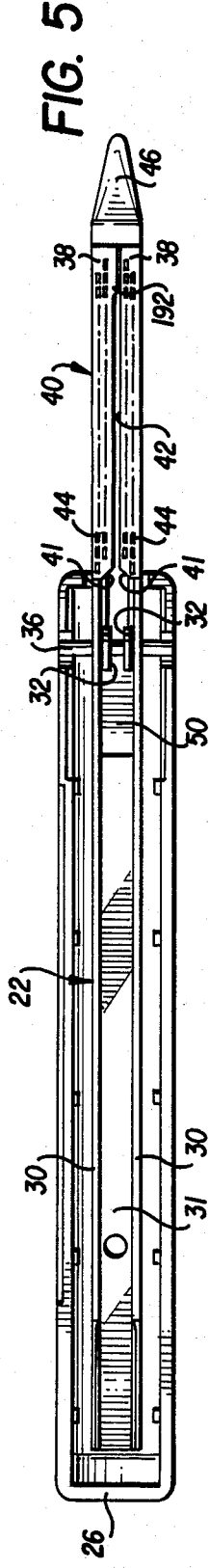
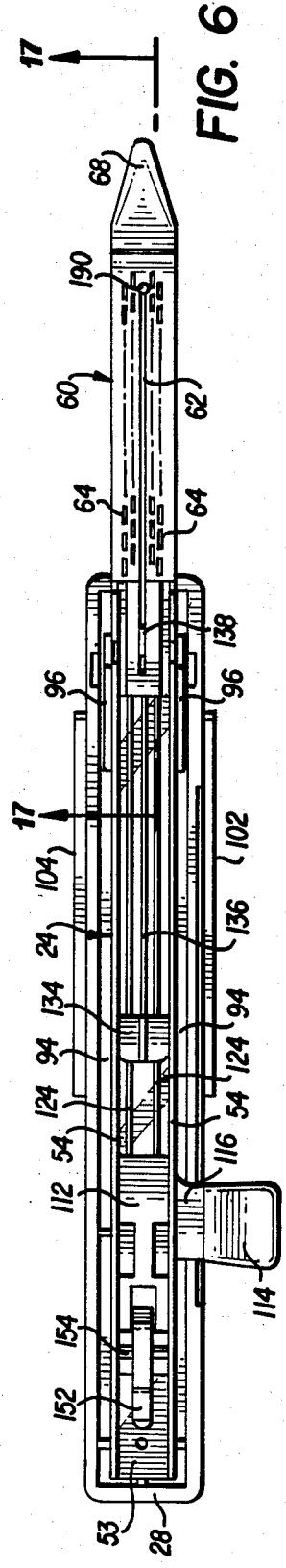
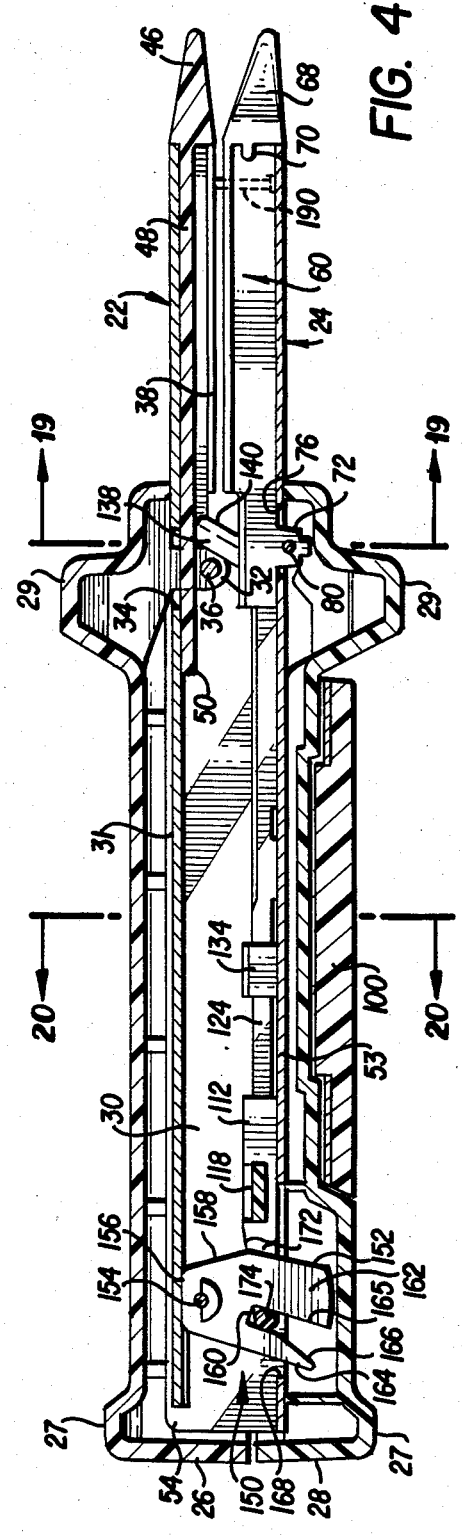

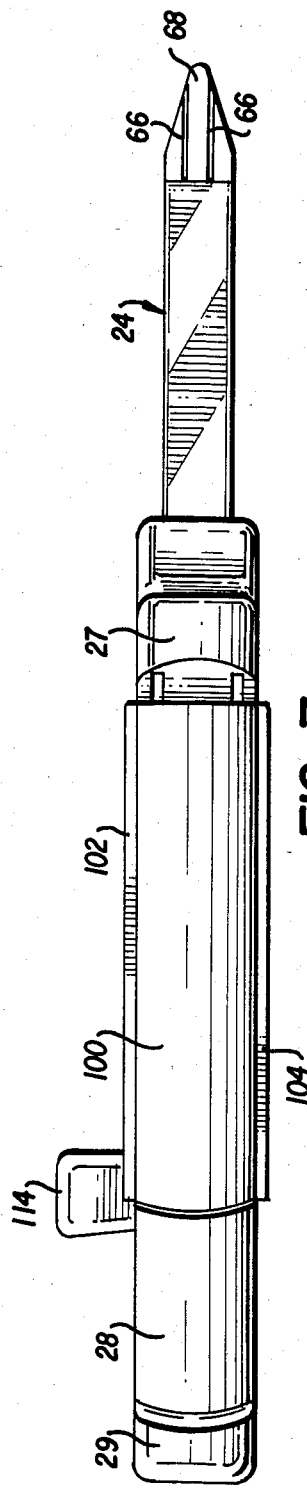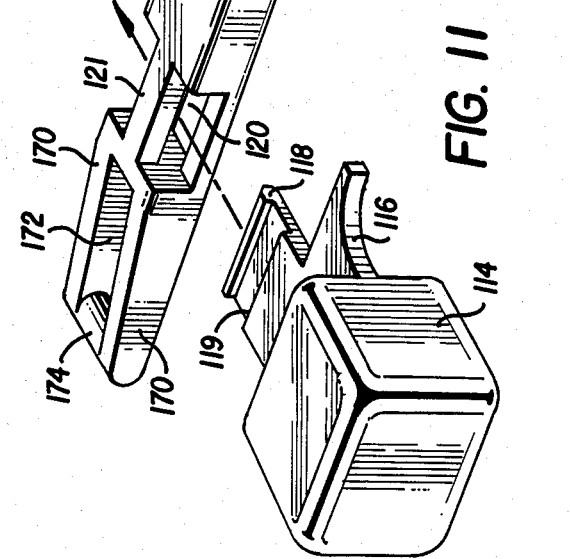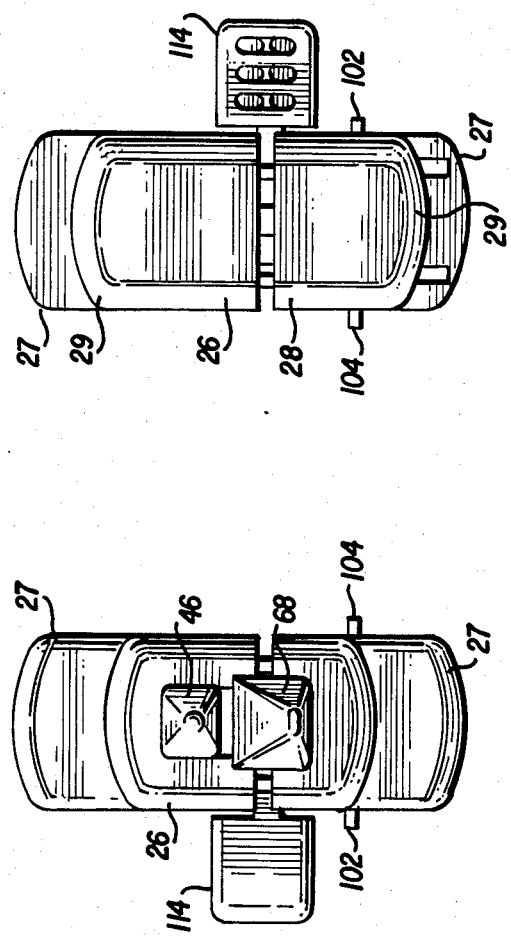
FIG. 7
FIG. 11
FIG. 9
FIG. 8

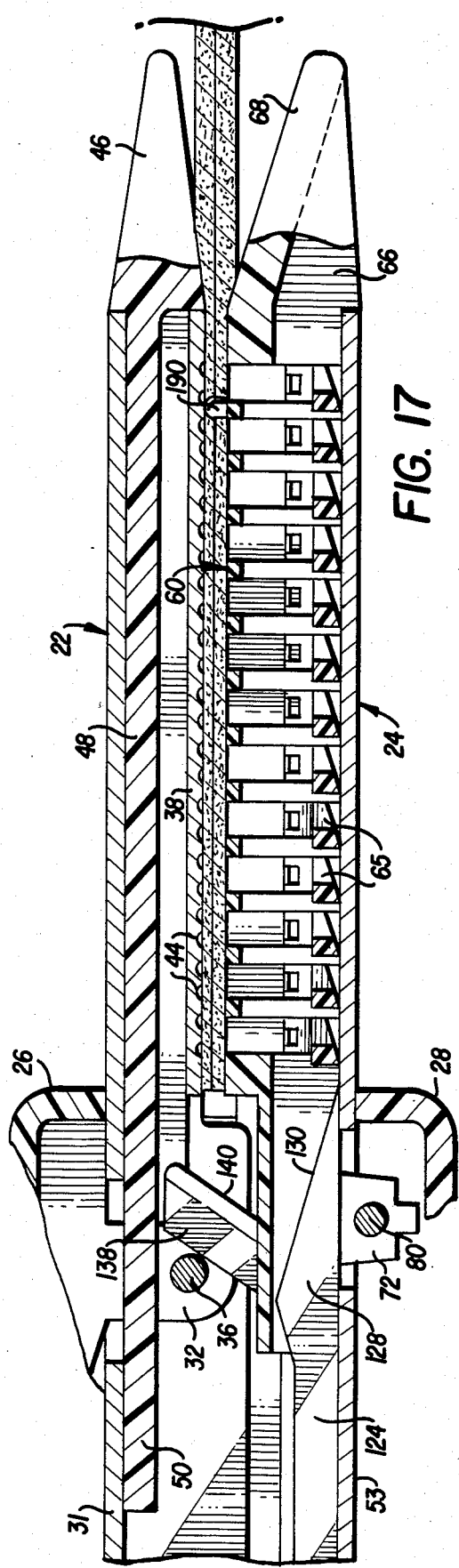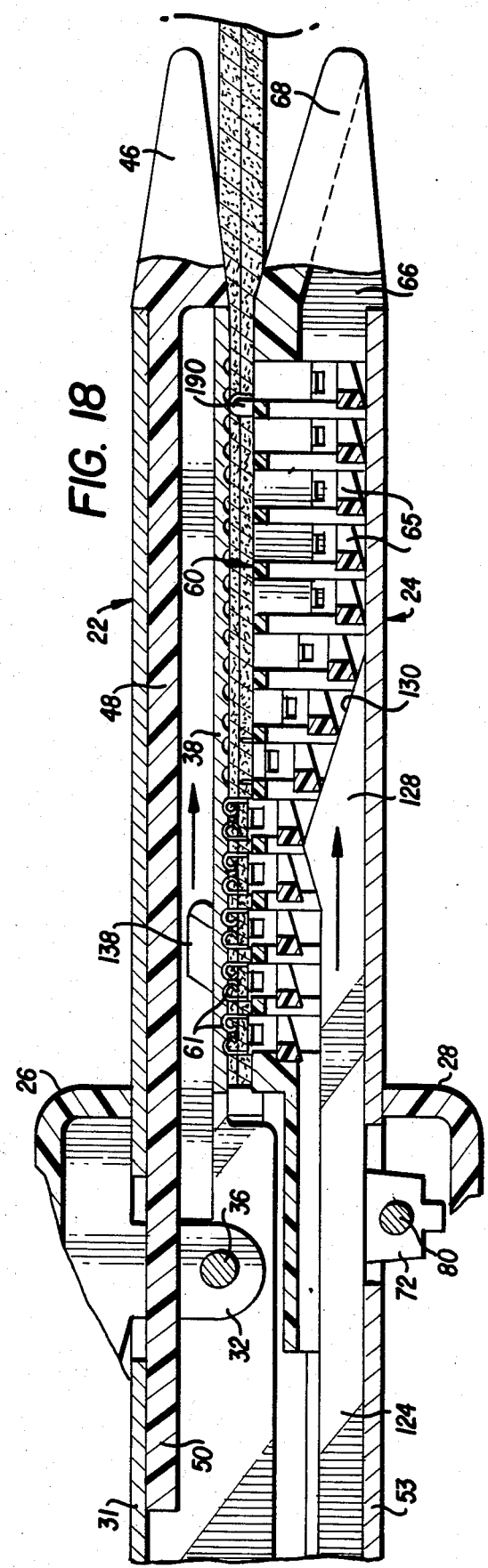

SURGICAL STAPLING INSTRUMENT WITH JAW CLAMPING MECHANISM

FIELD OF INVENTION

The present invention relates to a surgical stapling instrument and, more particularly, to a gastrointestinal anastomotic stapling instrument for producing one or more rows of staples which is adapted to resist the forces exerted on its jaw members when the staples are formed. Specifically, this invention relates to a linear anastomotic stapling instrument including a jaw clamping mechanism which applies clamping forces to its elongate jaw members to resist the forces exerted on the anvil and staple cartridge carrying portions of the jaw members when the staples are formed to permit uniform staple heights to be produced.

BACKGROUND AND PRIOR ART

In recent years, there has been an increasing tendency for surgeons to use stapling instruments to suture body organs and tissues such as lung, esophagus, stomach, duodenum and other body organs in the intestinal tract. The use of an appropriate stapling instrument in most instances performs a better job in less time and simplifies previously difficult surgical procedures such as gastrointestinal anastomoses.

In the prior art, the early linear two and four row cutting staplers were permanent instruments into which the staples were individually hand loaded. These staplers were very expensive, bulky, heavy and difficult to load and to clean for each surgical use. An example is disclosed in U.S. Pat. No. 3,315,105. An improvement of the permanent type surgical stapler was made by providing the basic stapling instrument with a presterilized disposable staple loading unit and with an optional knife for dividing the tissue simultaneously while forming the rows of staples. An example is disclosed in U.S. Pat. No. 3,499,591. However, this improvement mainly accomplished the saving of the time previously required to load the staples by hand. It was still necessary for the basic instrument to be disassembled, cleaned, reassembled and fitted with a new cartridge and anvil for each surgical procedure, in addition to the maintenance required of the stapling instrument itself. Another problem with this type of instrument is the tendency for the jaws to spread apart at the distal end after repeated use resulting in a substantial variation in the formed staple heights between the proximal and distal ends of the staple rows.

As hospital costs have continued to increase, it has become necessary to eliminate unnecessary work and develop more efficient techniques without compromise to the surgical procedure. Consequently, disposable stapling instruments of the type disclosed in U.S. Pat. No. 4,429,695 have been developed. In the disposable stapling instrument of this patent, an actuator and knife blade assembly provides local support to the stapler jaws in the region of the knife blade and pusher bar cams. However, this stapling instrument does not provide clamping forces simultaneously along the entire length of the anvil and staple cartridge carrying portions of the stapler jaws to resist the tendency of the jaws to separate when the staples are formed. Thus, there is the possibility that rows of non-uniform staple heights will be produced. If the tissue is stapled too tightly, the blood supply is compromised and the tissue may necrose. If stapled too loosely, the tissue may hemorrhage or, in the case of hollow organs such as intestine, may also leak. Thus, both too tightly and too loosely formed staples can cause serious problems and complications.

Typically, a linear anastomotic stapling instrument includes a pair of cooperating elongate jaw members, each adapted to be inserted into internal, tubular body organs to be anastomosed. One of the jaw members supports a staple cartridge with at least two laterally spaced rows of staples, and the other jaw member supports an anvil with staple-forming pockets aligned with the rows of staples in the cartridge. Generally, a single pusher bar and knife assembly is slidable longitudinally along the jaw members to sequentially eject staples from the cartridge via camming surfaces which activate a plurality of staple drivers carried by the cartridge and associated with the individual staples to close the staples against the anvil and form laterally spaced rows of staples in the tissue gripped between the jaw members. A knife blade which trails the pusher bars cuts the tissue along a line between the staple rows. Examples of such anastomotic stapling instruments are disclosed in U.S. Pat. Nos. 3,499,591 and 4,429,695. In neither instance is any provision made for application of clamping forces simultaneously along the entire portions of the jaw members which support the anvil and staple cartridge to resist the forces exerted when the staples are formed.

In the use of stapling instruments of the above type, relatively large forces are exerted in clamping the tissue to be fastened between the jaw members, ejecting the staples from the staple cartridge, driving the staples into the gripped tissue, and forming the staples against the anvil. Such forces tend to separate the jaw members vertically and to distort the jaw members laterally, with the result that the consistency of the formed staple height is diminished, or that the staples may sometimes miss the anvil completely. This problem is accentuated in the case of a disposable stapling instrument in which relatively lightweight disposable materials are used for the manufacture of the jaw members and other components. Thus, there is a need for a disposable stapling instrument which is capable of accurate alignment of the jaw members while the staple forming operation is performed, and which provides adequate support for its elongate jaw members to withstand the large forces encountered in the operation of the stapling instrument. In addition, there is a need for a stapling instrument which produces staple rows of uniform height in the tissue gripped between its jaw members.

SUMMARY OF INVENTION

The present invention achieves a surgical stapling instrument which overcomes the disadvantages of the prior art by incorporating an improved jaw clamping mechanism which applies clamping forces to its jaw members to resist the forces exerted on the anvil and staple cartridge carrying portions of the jaw members during the formation of the staples. Preferably, the stapling instrument includes a latching mechanism for latching the jaw members together at an intermediate position therealong adjacent to the staple and anvil carrying portions of the jaw members. The stapling instrument also includes a cam mechanism for urging the jaw members apart at a position remote from the latching mechanism to resist the forces exerted on the anvil and staple carrying portions of the jaw members when the staples are formed.

In accordance with the invention, a surgical stapling instrument comprises first and second cooperating elongate jaw members, one of the jaw members including stapling carrying means adapted to receive a plurality of staples arranged in at least one row, and the other jaw member including anvil means adapted to form the staples, pusher means for driving the staples from the staple carrying means into tissue gripped between the jaw members and forming the staples against the anvil means to produce at least one row of staples in the tissue, knife means for cutting the tissue gripped between the jaw members along a line adjacent to the row of staples, and jaw clamping means for applying clamping forces to the jaw members to resist the forces exerted on the staple carrying means and anvil means when the staples are formed. Preferably, the jaw clamping means is adapted to apply clamping forces to the jaw members which urge the staple carrying means and anvil means together during the formation of the staples against the anvil means to produce a uniform staple height.

In a preferred embodiment, the jaw clamping means includes means for latching the jaw members together at an intermediate position therealong adjacent to the staple carrying means and the anvil means, and means for urging the jaw members apart at a position remote from the latching means to resist the forces exerted on the staple carrying means and the anvil means when the staples are formed. Preferably, the means for urging the jaw members apart comprises cam means mounted on one of the jaw members and engageable with the other jaw member for moving the jaw members apart to urge the staple carrying means and the anvil means together. The cam means comprises a cam member pivotally mounted on one of the jaw members at a position remote from the latching means. The cam member is pivotable from a first inoperative position to a second operative position to move the jaw members apart at the remote position. The cam member includes a first lower cam surface for engaging the other jaw member with the cam member disposed in its second operative position. At least one of the jaw members is flexible to permit portions of the jaw members to bend apart at the remote position. When the cam member pivots from its inoperative position to its operative position, the portions of the jaw members at the remote position bend apart to urge the anvil and staple carrying portions of the jaw members together.

Preferably, the cam means is operable by the pusher means prior to the formation of the staples to urge the staple carrying means and anvil means together. Actuator means is provided for initially actuating the pusher means while the knife means remains stationary to actuate the cam means and for subsequently actuating the pusher means and the knife means simultaneously to drive the staples into the tissue and to cut the tissue. As a result, the initial force required to operate the stapling instrument is minimized. In addition, spacer means is mounted on one of the jaw members for maintaining a predetermined gap between the staple carrying means and the anvil means to produce a uniform staple height when the staples are formed.

The present invention is embodied in a linear gastrointestinal stapling instrument provided with first and second elongate jaw members for gripping tissue therebetween. A staple cartridge carrying at least two laterally spaced longitudinal rows of staples is mounted on a front portion of one of the jaw members, and a staple forming anvil is provided on a front portion of the other jaw member. A pusher bar and knife blade assembly is slidably mounted for longitudinal movement relative to the jaw members. The pusher bar and knife blade assembly includes pusher means for driving the staples from the staple cartridge into tissue gripped between the jaw members and forming the staples against the anvil to produce a pair of laterally spaced staple rows in the tissue, and knife means for cutting the tissue gripped between the jaw members along a line between the staple rows. The stapling instrument includes jaw clamping means for urging the front portions of the jaw members together to clamp the staple cartridge and the anvil against the tissue gripped between the jaw members during the formation of the staples. The jaw clamping means is embodied as means for latching the jaw members together at an intermediate position therealong adjacent to the staple cartridge and the anvil, and means for urging the rear portions of the jaw members apart at a position remote from the latching means to urge the front portions of the jaw members together to resist the forces exerted on the staple cartridge and the anvil when the staples are formed.

In a preferred embodiment, a cam mechanism is mounted on one of the jaw members which is engageable with the other jaw member for moving the rear portions of the jaw members apart to urge the staple cartridge and anvil together. Preferably, a cam member is pivotally mounted on one of the jaw members at a position remote from the latching means. The cam member is pivotable from a first inoperative position to a second operative position to move the rear portions of the jaw members apart and to urge the front portions of the jaw members together. The cam member includes a first lower cam surface for engaging the other jaw member with the cam member disposed in its first inoperative position and a second higher cam surface for engaging the jaw member with the cam member disposed in its second operative position. Preferably, the cam member is operable by the pusher means to move from its inoperative position to its operative position when the pusher means is advanced and to return from its operative position to its inoperative position when the pusher means is retracted. At least one of the jaw members is flexible to permit its rear portion to bend away from the rear portion of the other jaw member and its front portion to bend toward the front portion of the other jaw member to urge the staple cartridge and anvil together. In addition, spacer means is mounted on one of the jaw members for maintaining a predetermined gap between the staple cartridge and anvil.

Preferably, the pusher bar and knife assembly includes a pusher block slidably mounted for longitudinal movement along one of the jaw members and provided with a pair of staple pusher bars adapted to slide into the staple cartridge, and a knife block slidably mounted for longitudinal movement along one of the jaw members and provided with a knife blade adapted to slide into the staple cartridge between the staple pusher bars. The cam mechanism is operable by the pusher block prior to the formation of the staples to urge the staple cartridge and anvil together. Actuator means is provided for initially advancing the pusher block toward the staple cartridge while the knife block remains stationary to actuate the cam mechanism and to initially move the pusher bars into the staple cartridge and for subsequently advancing the knife block toward the staple cartridge upon engagement by the pusher block to move the pusher bars and knife blade simultaneously into the staple cartridge. In the preferred embodiment, the cam mechanism is actuated by the pusher block prior to engagement of the pusher block with the knife block to reduce the force initially required to operate the stapling instrument. Preferably, the knife block is adapted to slidably receive the pusher bars to permit the pusher block to initially slide relative to the knife block when the pusher block is advanced to actuate the cam mechanism and when the pusher block is retracted after the staples are formed. The pusher bars are adapted to engage the knife block as the pusher block is retracted to withdraw the knife blade from the staple cartridge.

The invention provides an improved linear gastrointestinal anastomotic stapling instrument which advantageously incorporates a cam mechanism for urging the staple cartridge and anvil together during the formation of the staples. These additional clamping forces resist the forces exerted on the staple cartridge and anvil when the staples are formed which would otherwise tend to spread the staple cartridge and anvil apart and result in the forming of closed staples of non-uniform height. In addition, the actuation of the cam mechanism by a two-stage pusher bar and knife blade assembly minimizes the initial force required to actuate the stapling instrument.

BRIEF DESCRIPTION OF DRAWINGS

FIG. 2 is a side elevation showing the anastomotic stapling instrument partially disassembled with its upper anvil carrying jaw member detached from its lower staple cartridge carrying jaw member;

FIG. 3 is a side elevation showing the anastomotic stapling instrument in its assembled configuration;

FIG. 4 is a side elevation, partially in section, of the anastomotic stapling instrument showing a cam mechanism for urging the rear portions of the upper and lower jaw members apart;

FIG. 5 is a bottom view of the anvil carrying jaw member of the anastomotic stapling instrument;

FIG. 6 is a top view of the staple cartridge carrying jaw member of the anastomotic stapling instrument;

FIG. 7 is a bottom view of the anastomotic stapling instrument;

FIG. 8 is a front end view of the anastomotic stapling instrument;

FIG. 9 is a rear end view of the anastomotic stapling instrument;

FIG. 10 is an enlarged perspective view of a pusher bar and knife blade assembly of the anastomotic stapling instrument;

FIG. 11 is an enlarged perspective view of a pusher block and an actuator knob which are components of the pusher bar and knife blade assembly of the anastomotic stapling instrument;

FIG. 17 is an enlarged, partially cutaway view of the anvil and staple cartridge carrying jaw members of the anastomotic stapling instrument;

FIG. 18 is an enlarged, partially cutaway view of the anvil and staple cartridge carrying jaw members illustrating the operation of the pusher bar and knife blade assembly;

DETAILED DESCRIPTION OF PREFERRED EMBODIMENT

Figure 1:
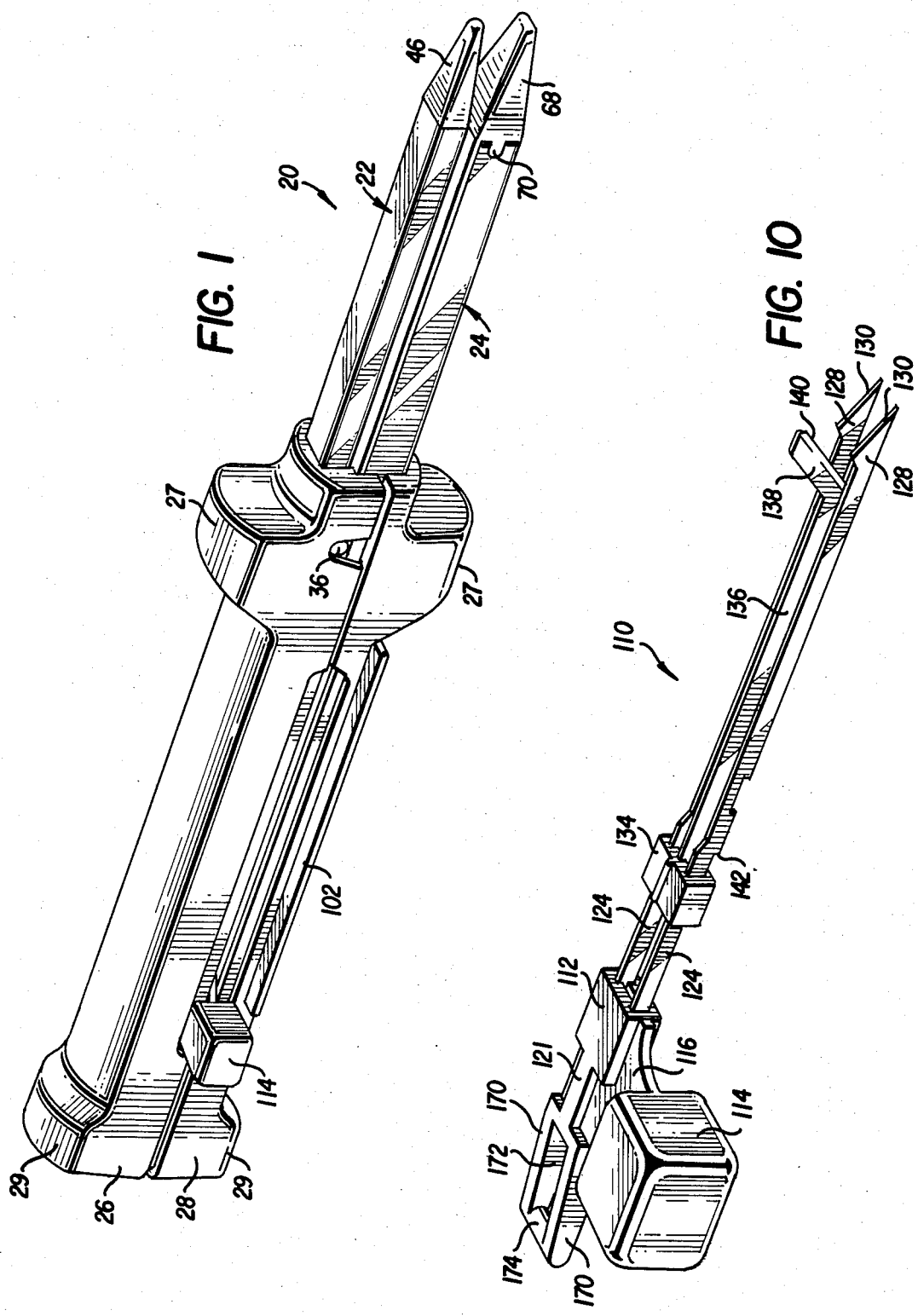
FIG. 1 is an overall perspective view of a linear anastomotic stapling instrument embodying the principles of the present invention.

Referring to FIGS. 1 and 2, the present invention is embodied in a linear anastomotic stapling instrument, generally 20, comprising an upper elongated anvil carrying jaw member 22 and a lower elongated staple cartridge carrying jaw member 24. Upper anvil carrying jaw member 22 is supported by a handle 26 with a front portion of the jaw member extending forwardly therefrom. Lower staple cartridge carrying jaw member 24 is supported by a handle 28 with a front portion of the jaw member extending forwardly therefrom. As shown in FIG. 3, upper handle 26 and lower handle 28 are suitably shaped to form a hand grip to facilitate the handling and operation of the stapling instrument by a surgeon. An enlarged front protrusion 27 and a small rear protrusion 29 are provided on each handle for this purpose. Preferably, handles 26 and 28 are made of plastic of other lightweight material, while jaw members 22 and 24 are made of stainless steel or other similar material.

As shown in FIG. 5, upper jaw member 22 comprises a one-piece elongated channel-shaped frame including a pair of opposed, elongated side walls 30 connected by a top wall 31. Upper handle 26 includes a pair of depending ears 32 located inside the upper handle adjacent to its front end. Upper jaw member 22 includes a slot 34 (FIG. 4) formed at an intermediate position along its top wall 31 through which depending ears 32 project downward. A latch pin 36 extends through circular holes formed in side walls 30 of upper jaw member 22 and through circular holes formed in depending ears 32 to pivotally connect the upper jaw member to upper handle 26.

Referring to FIG. 5, the front portion of upper jaw member 22 is provided with a pair of elongated inwardly extending flanges 38 which define an anvil 40 of the stapling instrument. Flanges 38 are separated by a central longitudinal slot 42 which extends along the entire length of anvil 40. At the proximal end of central slot 42, the flanges 38 are provided with inwardly sloped guide surfaces 41. Each flange 38 is also provided with two longitudinal rows of uniformly spaced staple-forming pockets 44.

Referring to FIGS. 4 and 5, a tapered anvil tip 46 is mounted at the front of anvil carrying jaw member 22 to facilitate the insertion of the jaw member into hollow, tubular body organs. Anvil tip 46 includes an elongated body 48 (FIG. 4) which is inserted through the longitudinal passageway above anvil 40 defined by side walls 30 and flanges 38 of the upper jaw member. This elongated body 48 extends between depending ears 32 above latch pin 36 and includes an enlarged rear portion 50 located behind ears 32 to hold anvil tip 46 in place on upper jaw member 22.

Referring to FIGS. 2 and 6, lower cartridge carrying jaw member 24 comprises a one-piece elongated channel-shaped frame including a pair of opposed, elongated side walls 52 connected by a bottom wall 53. Along the rearward portion of lower jaw member 24, a pair of spaced, elongated upstanding side flanges 54 (FIG. 2) extend upward from its opposed side walls 52. As shown in FIGS. 5 and 6, the width of lower jaw member 24 between its side flanges 54 is greater than the width of upper jaw member 22 between its side walls 30 to permit the rear portion of the upper jaw member to be received between side flanges 54 of the lower jaw member when the stapling instrument is assembled for operation. As shown in FIG. 2, each side flange 54 of lower jaw member 24 includes a vertical notch 56 located in alignment with latch pin 36 on upper jaw member 22. When upper jaw member 22 and lower jaw member 24 are assembled, the opposite ends of latch pin 36 are received in notches 56.

Figure 15:
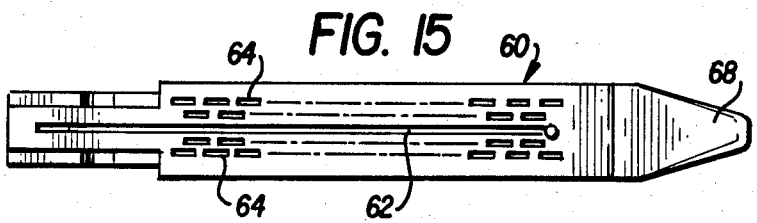
FIG. 15 is an enlarged top view of the staple cartridge of the anastomotic stapling instrument.
Figure 16:
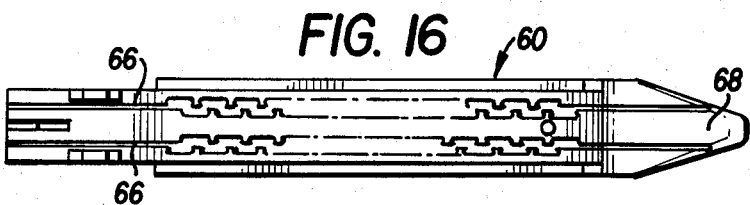
FIG. 16 is an enlarged bottom view of the staple cartridge of the anastomotic stapling instrument.

As shown in FIGS. 2 and 6, lower jaw member 24 supports a staple cartridge 60 which is adapted to receive a plurality of surgical staples 61 (FIG. 18) arranged in at least two laterally spaced longitudinal rows. Staple cartridge 60 is mounted at the front portion of lower jaw member 24 between its side walls 52. Staple cartridge 60 is divided longitudinally by a central, elongated slot 62 (FIG. 6) which extends from the proximal end of the cartridge toward its distal end. Preferably, a plurality of staple openings 64 formed in staple cartridge 60 is arranged in two pairs of laterally spaced rows, with each pair of rows disposed on opposite sides of central longitudinal slot 62. A plurality of surgical staples 61 (FIG. 18) are mounted within openings 64 of cartridge 60. As shown in FIG. 6, the staple openings 64 in adjacent rows are staggered to provide more effective stapling of the tissue when the instrument is operated. Referring to FIGS. 15 and 16, staple cartridge 60 includes a pair of longitudinal slots 66 located on opposite sides of elongated central slot 62 and disposed between the staggered rows of openings 64 on each side of the central slot. Each longitudinal slot 66 extends from the proximal end of cartridge 60 towards its distal end.

As shown in FIG. 17, a plurality of staple drivers 65 is slidably mounted in staple openings 64 for actuating the staples 61 which are loaded into staple cartridge 60. Referring to FIG. 6, each staple driver 65 is designed to simultaneously actuate two staples 61 located in the adjacent rows provided in staple cartridge 60. Thus, a first set of staple drivers 65 is provided for actuating the staples 61 in the staggered rows located on one side of central longitudinal slot 62, and a second set of staple drivers 65 is provided for actuating the staples 61 in the pair of adjacent rows located on the other side of central longitudinal slot 62.

Figure 14:
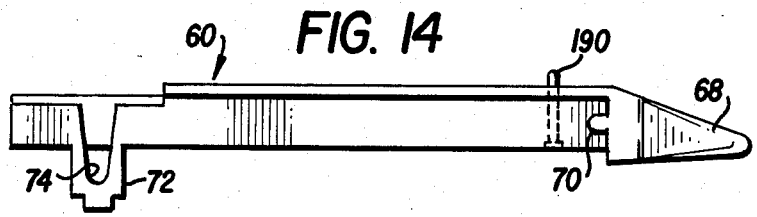
FIG. 14 is an enlarged side view of the staple cartridge of the anastomotic stapling instrument.
Figure 19:
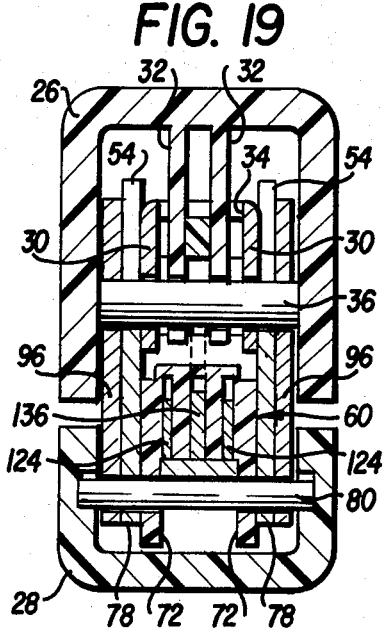
FIG. 19 is an enlarged vertical section of the anastomotic stapling instrument taken along line 19—19 of FIG. 4.

As shown in FIGS. 2 and 3, the front or distal end of staple cartridge 60 includes a tapered tip 68 to facilitate the insertion of lower jaw member 24 into a hollow, tubular body organ. Immediately behind its tapered tip 68, staple cartridge 60 is provided with a pair of rearwardly extending protrusions 70 (one shown in FIG. 14) which are received in corresponding notches provided in side walls 52 of lower jaw member 24. At the rear of staple cartridge 60, a pair of depending arms 72 extends downwardly from the cartridge. Each arm 72 is notched to provide a side opening 74. When cartridge 60 is assembled on lower jaw member 24, its protrusions 70 are received in corresponding notches provided at the front ends of side walls 52 and its depending arms 72 extend downwardly through an opening 76 (FIG. 4) formed in bottom wall 53 of jaw member 24. Lower jaw member 24 includes a pair of depending ears 78 (FIG. 19) extending downwardly from its side walls 52 on opposite sides of opening 76. A pivot pin 80 extends through holes formed in depending ears 78 of lower jaw member 24 and through side openings 74 of depending arms 72 on staple cartridge 60 to fasten the staple cartridge to the lower jaw member.

Referring to FIG. 2, the stapling instrument 20 includes a latching mechanism, generally 90, for latching upper jaw member 22 and lower jaw member 24 together at an intermediate position along the jaw members. Preferably, jaw members 22 and 24 are latched together at a position adjacent to the proximal ends of anvil 40 and staple cartridge 60. In the preferred embodiment, latching mechanism 90 comprises a latch arm 92 (FIG. 2) pivotally connected to lower jaw member 24 via pivot pin 80 (FIG. 4). Latch arm 92 is channel-shaped in configuration and includes a pair of opposed, elongated side walls 94 (FIG. 6) which are spaced apart by a distance sufficient to span side walls 52 of lower jaw member 24. Each side wall 94 of latch arm 92 includes an upwardly and forwardly extending hook member 96 provided with a forwardly facing slot 98 for receiving latch pin 36. A shroud 100 is mounted on the lower surface of latch arm 92. When latch arm 92 is closed, as shown in FIG. 3, shroud 100 is aligned with the bottom of lower handle 28 to facilitate the handling and operation of stapling instrument 20 by the surgeon. Preferably, shroud 100 is made of plastic or other lightweight material, while latch arm 92 is made of stainless steel. As shown in FIG. 7, shroud 100 includes elongated flanges 102 and 104 extending outwardly from its opposite sides which serve as fingergrips to enable latch arm 92 to be pivoted downward from its latched to its unlatched position. When latch arm 92 is moved to its closed or latched position, the surfaces of slots 98 of hook members 96 cooperate with latch pin 36, acting as an over-center latch to maintain latch arm 92 in its latched position.

Referring to FIGS. 6 and 10, the preferred embodiment of stapling instrument 20 includes an improved pusher bar and knife blade assembly, generally 110, which is slidably mounted for longitudinal movement relative to upper and lower jaw members 22 and 24, respectively, for driving staples 61 from staple cartridge 60 into tissue gripped between the jaw members, forming staples 61 against anvil 40, and cutting the tissue along a line between the rows of staples formed in the tissue. Pusher bar and knife blade assembly 110 includes a pusher block 112 (FIG. 6) which is slidably received within the lower channel-shaped jaw member 24 between its upstanding side flanges 54. As shown in FIG. 11, pusher block 112 is attached to an actuator knob 114 by a flange 116 which includes a laterally projecting finger 118 provided with a longitudinally extending notch 119 on its top surface. Finger 118 is snap-fitted into a lateral slot 120 formed in pusher block 112 to locate notch 119 underneath a longitudinal locking bar 121 to secure pusher block 112 and actuator knob 114 together. Flange 116 of actuator knob 114 extends through and rides along an elongated slot 122 (FIG. 2) formed in one side flange 54 of lower jaw member 24.

Figure 21:
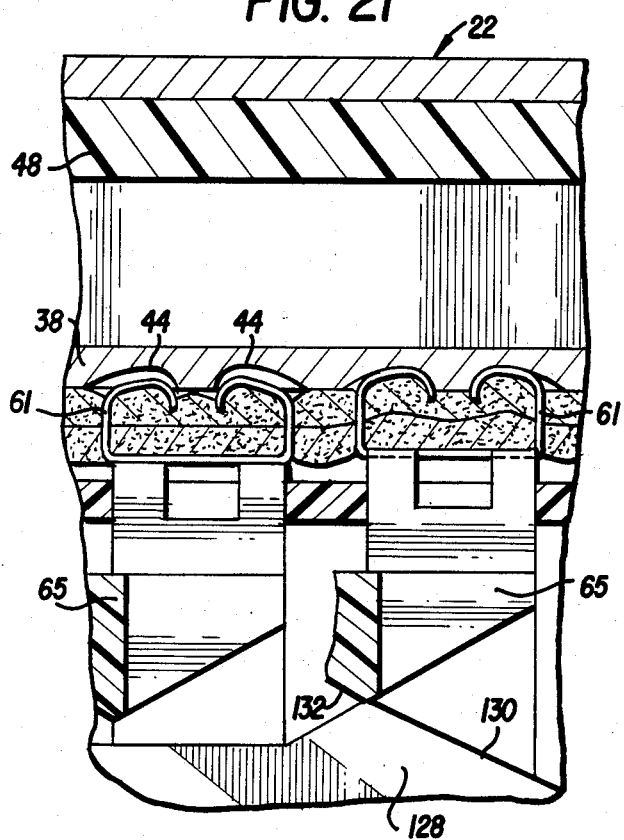
FIG. 21 is an enlarged section of a portion of the anvil and staple cartridge shown in FIG. 18.

The pusher bar and knife blade assembly 110 includes a pair of staple pusher bars 124 (FIG. 10) projecting forwardly from pusher block 112 and slidably received in elongated slots 66 (FIG. 16) of staple cartridge 60. Pusher block 112 is provided with a pair of vertical slots 126 (FIG. 11) in which pusher bars 124 are secured. As shown in FIG. 10, the front end of each staple pusher bar 124 is provided with a wedge-shaped tip 128 which defines an inclined cam surface 130 for engaging staple drivers 65 as pusher bars 124 are advanced into staple cartridge 60. As shown in FIG. 21, each staple driver 65 is provided with a sloped surface 132 oriented at the same angle as cam surface 130 of each staple pusher bar 124 to provide a flat, sliding contact between the surfaces.

Referring to FIGS. 6 and 10, the pusher bar and knife blade assembly 110 includes a knife block 134 which is slidably mounted for longitudinal movement along lower jaw member 24 between its upstanding side flanges 54. Knife block 134 includes a knife support bar 136 which extends forwardly into central longitudinal slot 62 of staple cartridge 60. An inclined knife blade 138 provided with a beveled cutting edge 140 is located at the front end of knife support bar 136. The beveled cutting edge of knife blade 138 is oriented at an angle relative to elongate jaw members 22 and 24 and is slidably received in central longitudinal slot 62 of staple cartridge 60.

Figure 20:
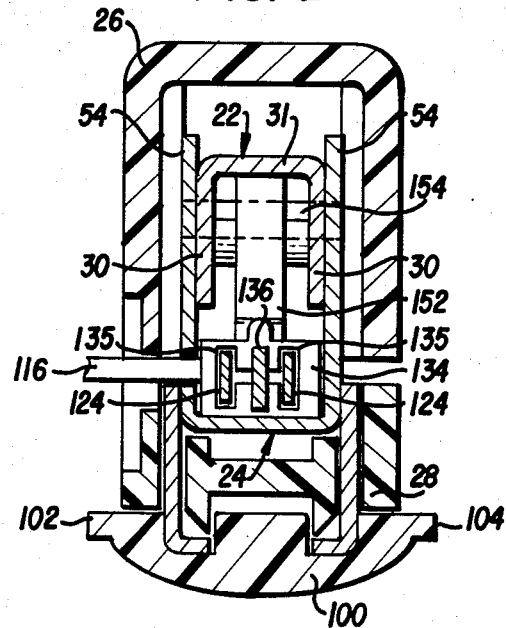
FIG. 20 is an enlarged vertical section of the anastomotic stapling instrument taken along line 20—20 of FIG. 4.

In the preferred embodiment of stapling instrument 20, knife block 134 includes a pair of longitudinal slots 135 (FIG. 20) extending therethrough which slidably receive staple pusher bars 124 to permit pusher block 112 to slide relative to the knife block. Accordingly, when pusher block 112 is advanced toward staple cartridge 60 by actuator knob 114, staple pusher bars 124 slide through knife block 134 which remains stationary until the pusher block moves into engagement with the knife block. After knife block 134 is engaged by pusher block 112, the knife block and pusher block advance simultaneously toward staple cartridge 60. As shown in FIG. 18, knife blade 138 is advanced through staple cartridge 60 along with staple pusher bars 124, forming staples 61 in the tissue gripped between the jaw members and cutting the tissue between the staple rows. Thereafter, when actuator knob 114 is retracted, pusher block 112 initially slides staple pusher bars 124 backward through knife block 134 which remains stationary. Each staple pusher bar 124 includes an offset portion 142 which moves into engagement with knife block 134 after staple pusher bars 124 are withdrawn by a predetermined distance. With offset portions 142 of staple pusher bars 124 engaging knife block 134, pusher block 112 and knife block 134 are simultaneously retracted by actuator knob 114 to return pusher bars 124 and knife blade 138 to the start position.

In accordance with the invention, stapling instrument 20 is provided with jaw clamping means for applying clamping forces to the jaw members to urge staple cartridge 60 and anvil 40 together during the formation of staples 61. The jaw clamping means includes means for urging the jaw members apart at a position remote from the latching mechanism to resist the forces exerted on staple cartridge 60 and anvil 40 when staples 61 are formed. In the preferred embodiment, a cam means is mounted on one of the jaw members and engageable with the other jaw member for moving said jaw members apart at the remote position to urge staple cartridge 60 and anvil 40 together. Preferably, a cam member is pivotally mounted on one of the jaw members at a position remote from the latching mechanism. The cam member is pivotable from a first inoperative position to a second operative position to move the remote ends of the jaw members apart. The cam member is operable by pusher block 112 of pusher bar and knife blade assembly 110 to move to its operative position when the pusher block is advanced and to return to its inoperative position when the pusher block is retracted.

Figure 12:
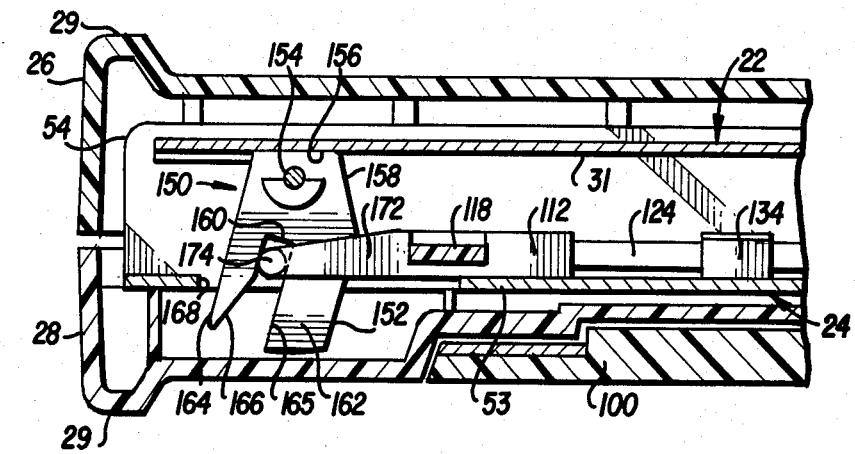
FIG. 12 is an enlarged elevation, partially in section, of the rear portion of the anastomotic stapling instrument illustrating the cam mechanism in its inoperative position.
Figure 13:
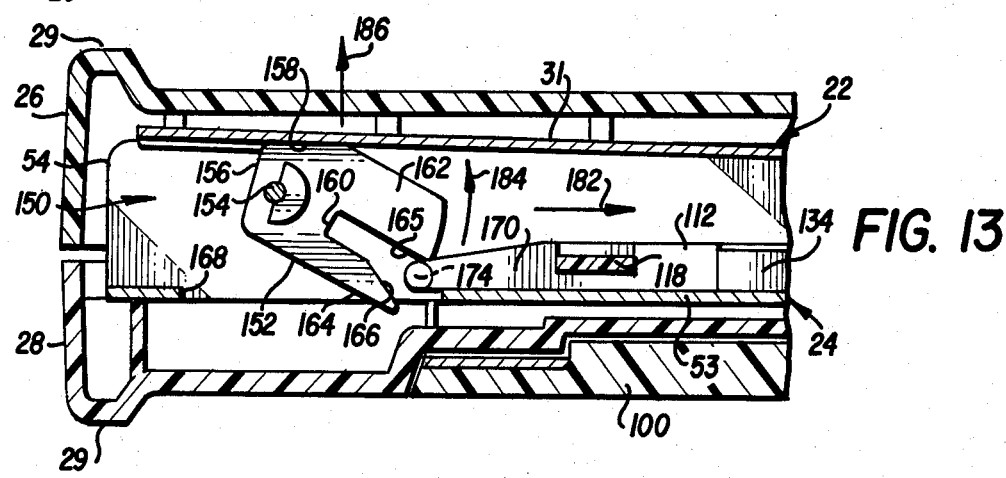
FIG. 13 is an enlarged elevation, partially in section, of the rear portion of the anastomotic stapling instrument illustrating the cam mechanism in its operative position.

In the preferred embodiment of the stapling instrument 20, a cam mechanism, generally 150, is located adjacent to the rear end of lower jaw member 24, as shown in FIG. 4. Cam mechanism 150 includes a cam member 152 pivotally mounted on a transverse pivot pin 154 extending between upstanding side flanges 54 of lower jaw member 24. Cam member 152 includes a first lower cam surface 156 for engaging top wall 31 of upper jaw member 22 with cam 152 in its first inoperative position (FIG. 12) and a second higher cam surface 158 for engaging the top wall 31 of upper jaw member 22 with cam 152 disposed in its second operative position (FIG. 13). First cam surface 156 is arranged to maintain upper and lower jaw members substantially parallel with cam 152 in its inoperative position. Second cam surface 158 is arranged to raise the rear end of upper jaw member 22 by approximately 0.125 inch (3.2 mm) when cam 152 pivots from its inoperative position to its operative position. In addition, upper jaw member 22 is sufficiently flexible to permit the rear portion of upper jaw member 22 to bend upward away from lower jaw member 24 when cam member 152 is moved from its inoperative position to its operative position.

As shown in FIG. 4, cam member 152 includes a radially extending notch 160 which divides the cam into a large front finger 162 and a small rear finger 164. Front cam finger 162 includes a flat, rearwardly facing surface 165, and rear cam finger 164 includes a sloped, forwardly facing surface 166. With cam 152 in its inoperative position, front cam finger 162 and rear cam finger 164 extend downwardly through an elongated slot 168 formed in bottom wall 53 of lower jaw member 24.

In the preferred embodiment, cam member 152 is operable by pusher block 112 to move from its inoperative position to its operative position when the pusher block is advanced. As shown in FIG. 11, pusher block 112 includes a pair of rearwardly extending arms 170 which are spaced apart to define a gap 172 therebetween. The rear ends of arms 170 are connected by a cam actuator pin 174 which extends across gap 172. Referring to FIGS. 4 and 11, with cam member 152 disposed in its inoperative position, front cam finger 162 extends through gap 172 between arms 170 of pusher block 112, while cam actuator pin 174 is received in notch 160 between front finger 162 and rear finger 164 of the cam member.

. As shown in FIG. 12, with cam member 152 disposed in its first inoperative position, top wall 31 of upper jaw member 22 rests on first cam surface 156 of the cam member. With cam member 152 in its inoperative position, top wall 31 of upper jaw member 22 is substantially parallel to bottom wall 53 of lower jaw member 24. In addition, pusher block 112 is located in its start position spaced rearwardly from knife block 134. When pusher block 112 is advanced, as indicated by arrow 182 (FIG.

13), cam actuator pin 174 engages rear surface 165 of front cam finger 162 to rotate cam member 152 in a counter-clockwise direction, as indicated by arrow 184, to pivot the cam member to its second operative position and move its second cam surface 158 into engagement with top wall 31 of upper jaw member 22. With cam member 152 pivoted to its operative position, the top wall 31 of upper jaw member 22 is bent upwardly, as indicated by arrow 186, away from bottom wall 53 of lower jaw member 24. The cam member applies forces to upper jaw member 22 and lower jaw member 24 which bend the rear portions of the jaw members apart. As a result of the bending the rear portions of upper jaw member 22 and lower jaw member 24 apart, additional clamping forces are applied to the front portions of upper jaw member 22 and lower jaw member 24 to clamp anvil 40 and staple cartridge 60 against the tissue gripped between the jaw members. Thus, anvil 40 and staple cartridge 60 are urged together to resist the forces exerted on the anvil and staple cartridge when pusher bar and knife blade assembly 110 is advanced to form staples 61 and cut the tissue.

Referring to FIG. 13, when pusher block 112 is retracted after staples 61 are formed, cam actuator pin 174 engages sloped surface 166 of rear cam finger 164 to pivot cam member 152 in a clockwise direction. As cam actuator pin 174 moves along sloped surface 166 into notch 160, cam member 152 pivots in a clockwise direction and returns to its first inoperative position (FIG. 12) with its first cam surface 156 in engagement with top wall 31 of upper jaw member 22. As a result, the forces exerted on the rear portions of upper jaw member 22 and lower jaw member 24 by cam 152 are released and top wall 31 of upper jaw member 22 returns to a substantially parallel relationship with bottom wall 53 of lower jaw member 24. Similarly, the clamping forces applied to the front portions of jaw members 22 and 24 are released to unclamp anvil 40 and staple cartridge 60.

The preferred embodiment of stapling instrument 20 includes spacer means mounted on one of the jaw members for maintaining a predetermined gap between staple cartridge 60 and anvil 40 of the stapling instrument. Referring to FIGS. 4 and 6, this spacer means is embodied as a spacer pin 190 mounted adjacent to the distal end of staple cartridge 60. Spacer pin 190 extends vertically upward from bottom wall 53 of lower jaw member 24 through staple cartridge 60 and projects upwardly from the top of the staple cartridge by a predetermined distance. As shown in FIG. 5, one flange 38 of anvil 40 includes a flange section 192 adjacent to its distal end for engaging spacer pin 190. With the stapling instrument assembled for operation (FIG. 4), spacer pin 190 engages flange section 192 to maintain a predetermined gap between anvil 40 and staple cartridge 60.

In the operation of stapling instrument 20, the tissue to be stapled and cut must be initially placed between jaw members 22 and 24 and clamped by the jaw members. Thus, handles 26 and 28 are unlatched by pivotal movement of latch arm 92 downward to its unlatched position (FIG. 2). As a result, the opposite ends of latch pin 36 are disengaged from slots 98 formed in hook members 96 of latching arm 92. Thereafter, upper and lower jaw members 22 and 24 can be separated by disengaging latch pin 36 from slots 56 formed in side flanges 54 of the lower jaw member.

Next, the tissue to be stapled and cut is placed on jaw members 22 and 24. For example, as shown in FIG. 17, a piece of tubular, intestinal tissue may be slipped onto the front portion of each jaw member. After the tissue is placed on the jaw member, stapling instrument 20 is reassembled. The reassembly can be accomplished by aligning latch pin 36 with vertical slots 56 formed in upstanding side flanges 54 of lower jaw member 24. Thereafter, side flanges 54 of lower jaw member 24 are positioned inside upper handle 26, spanning side walls 30 of upper jaw member 22, while the opposite ends of latch pin 36 are inserted into vertical slots 56. Finally, latch arm 92 is pivoted upward to its latched position (FIG. 3) with its cover 100 flush with the bottom of lower handle 28. As a result, hook members 92 are pivoted over latch pin 36 and slots 98 receive the opposite ends of the latch pin. Thus, upper jaw member 22 and lower jaw member 24 are latched together at an intermediate position therealong adjacent to anvil 40 and staple cartridge 60. In addition, spacer pin 190 engages flange section 192 of anvil 40 through the body tissue to maintain a predetermined gap between anvil 40 and staple cartridge 60.

After the tissue is clamped between the jaw members, stapling instrument 20 is fired by advancing actuator knob 114 to actuate the pusher bar and knife blade assembly 110. Initially, in the actuation of cam mechanism 150, pusher block 112 and pusher bars 124 (FIG. 4) are advanced, while knife block 134 remains stationary. Since only pusher block 112 and its pusher bars 124 are advanced to actuate cam member 152, the initial force required to operate stapling instrument 20 is minimized.

Referring to FIG. 12, during the initial advance of pusher block 112, pusher bars 124 slide through knife block 134 and the wedge-shaped tips 128 of the pusher bars begin to advance through slots 66 of staple cartridge 60. As pusher block 112 advances toward knife block 134, its cam actuator pin 174 engages rear surface 165 of front cam finger 162 to pivot cam 152 counter-clockwise, as indicated by arrow 184 of FIG. 13, to move the second cam surface 158 of the cam member into engagement with top wall 31 of upper jaw member 22. Cam member 152 applies forces to upper jaw member 22 and lower jaw member 24 which bend the rear portions of the jaw members apart. As a result, the rear end of top wall 31 of upper jaw member 22 is bent upward by approximately 0.125 inch (3.2 mm) relative to the rear end of bottom wall 53 of lower jaw member 24. The bending of the rear ends of jaw members 22 and 24 apart results in additional clamping forces on the front portions of the jaw members to clamp anvil 40 and staple cartridge 60 against the tissue gripped between the jaw members. These additional clamping forces tend to resist the forces exerted on anvil 40 and staple cartridge 60, while the tissue is cut and staples 61 are formed against anvil 40, to maintain the desired spacing between anvil 40 and staple cartridge 60 to produce formed staples 61 which are substantially uniform in height.

Referring to FIG. 13, after cam mechanism 150 is actuated, pusher block 112 subsequently engages knife block 134 to begin the longitudinal movement of knife block 134 toward staple cartridge 60. Preferably, the initial spacing between pusher block 112 and knife block 134 is arranged such that pusher block 112 engages knife block 134 slightly before cam member 152 arrives at its operative position. Alternatively, the initial spacing between pusher block 112 and knife block 134 can be arranged such that pusher block 112 initially engages knife block 134 after the movement of cam member 152 to its operative position is completed. When pusher block 112 engages knife block 134, the advance of knife blade 138 along central longitudinal slots 42 and 62 of anvil 40 and staple cartridge 60, respectively, is initiated. Thereafter, staple pusher bars 124 and knife blade 138 are advanced simultaneously to staple and cut the tissue gripped between anvil 40 and staple cartridge 60.

As pusher block 112 is advanced, staple pusher bars 124 are moved longitudinally along slots 66 provided in staple cartridge 60. The two wedge-like cam surfaces 130 of staple pusher bars 124 move through slots 66 into engagement with the sloped surfaces of staple drivers 65 to sequentially drive staples 61 from cartridge 60 and to form staples 61 into B-shaped configuration against anvil flanges 38. The cam surfaces 130 are located at the same distance from pusher block 112 to simultaneously actuate staple drivers 65 located on opposite sides of central longitudinal slot 62. At the same time, knife block 134 is advanced to move knife blade 138 through central longitudinal slot 42 of anvil 40 and through central longitudinal slot 62 of staple cartridge 60 to cut the tissue gripped between the jaw members. The additional clamping forces applied to the front portions of upper jaw member 22 and lower jaw member 24 via cam mechanism 150 tend to resist the forces exerted on anvil 40 and staple cartridge 60 when staples 61 are formed.

After pusher block 112 is fully advanced to form all of the staples in cartridge 60, the pusher block is retracted toward its start position by retraction of actuator knob 114. Initially, only pusher block 112 moves backward from staple cartridge 60 because staple pusher bars 124 slide through knife block 134 which remains stationary. When offset portions 142 of staple pusher bars 124 engage the front of knife block 134, the knife block is moved backward from staple cartridge 60 along with pusher block 112. As a result, staple pusher bars 124 and knife blade 138 are simultaneously retracted from staple cartridge 60 and anvil 40.

As pusher block 112 returns toward its start position, cam actuator pin 174 engages sloped surface 166 of rear cam finger 164 to pivot cam member 152 in a clockwise direction toward its inoperative position. Cam actuator pin 174 moves along sloped surface 166 into slot 160 between cam fingers 162 and 164 to return cam member 152 to its inoperative position. As a result, second cam surface 158 of cam member 152 is disengaged from the top wall of upper jaw member 22 and rear end of top wall 31 of upper jaw member 22 moves downward into engagement with first cam surface 156. At the same time, front cam finger 162 pivots downward into gap 172 between fingers 170 on pusher block 112, and both cam fingers 162 and 164 pivot downward into slot 168 formed in bottom wall 53 of lower jaw member 24. Thereafter, with cam member 152 in its inoperative position, latching arm 92 can be pivoted downward, as shown in FIG. 2, to permit upper jaw member 22 and lower jaw member 24 to be disassembled. At this point, the cut and stapled tissue can be removed from the jaw members.

The invention in its broader aspects is not limited to the specific details shown and described, and modifications may be made in the structure of the linear anastomosis stapling instrument disclosed without departing from the principles of the present invention.

We claim:

1. A surgical stapling instrument, comprising:
    first and second cooperating elongate jaw members, one of said jaw members including staple carrying means adapted to receive a plurality of staples arranged in at least one row, and said other jaw member including anvil means adapted to form said staples,
    pusher means for driving the staples from said staple carrying means into tissue gripped between said jaw members and forming the staples against said anvil means to produce at least one row of staples in the tissue,
    knife means for cutting the tissue gripped between said jaw members along a line adjacent to said row of staples,
    means for latching said jaw members together at an intermediate position therealong adjacent to said staple carrying means and said anvil means, and
    cam means mounted on one of said jaw members and engageable with said other jaw member at a position remoted from said latching means for moving said jaw members apart at said remote position to urge said staple carrying means and said anvil means together to resist the forces exerted thereon when the staples are formed.

2. The surgical stapling instrument of claim 1, wherein said cam means comprises:
    a cam member pivotally mounted on one of said jaw members at a position remote from said latching means, said cam member being pivotable from a first inoperative position to a second operative position to move said jaw members apart at said remote position.

3. The surgical stapling instrument of claim 2, wherein:
    said cam member includes a first lower cam surface for engaging said other jaw member with said cam member disposed in its first inoperative position and a second higher cam surface for engaging said other jaw member with said cam member disposed in its second operative position.

4. The surgical stapling instrument of claim 3, wherein:
    said cam member is operable by said pusher means to move from its inoperative position to its operative postion when said pusher means is actuated.

5. The surgical stapling instrument of claim 1, wherein:
    at least one of said jaw members is flexible to permit said one jaw member to bend away from said other jaw member at said remote position to urge said staple carrying means and said anvil means together.

6. The surgical stapling instrument of claim 1, wherein:
    said cam means is operable by said pusher means prior to the formation of said staples to urge said staple carrying means and said anvil means together.

7. The surgical stapling instrument of claim 6, which includes:
    actuator means for initially actuating said pusher means while said knife means remains stationary to actuate said cam means and for subsequently actuating said pusher means and said knife means simultaneously to drive the staples into the tissue and to cut the tissue.

8. The surgical stapling instrument of claim 1, which includes:

spacer means mounted on one of said jaw members for maintaining a predetermined gap between said staple carrying means and said anvil means.

9. A surgical stapling instrument, comprising:

first and second cooperating elongate jaw members, one of said jaw members including a staple cartridge mounted at a front portion of said jaw member and adapted to receive at least two laterally spaced longitudinal rows of staples, and said other jaw member including an anvil mounted at a front portion of said jaw member and adapted to form said staples, a pusher bar and knife assembly slidable longitudinally relative to said elongate jaw members, said assembly including pusher means for driving the staples from said staple cartridge into tissue gripped between said jaw members and forming the staples against said anvil to produce a pair of laterally spaced staple rows in the tissue, and knife means for cutting the tissue gripped between said jaw members along a line between said staple rows, means for latching said jaw members together at an intermediate position therealong adjacent to said staple cartridge and said anvil, and cam means mounted on one of said jaw members and engageable with said other jaw member at a position remote from said latching means for moving said rear portions of said jaw members apart to urge said staple carrying means and said anvil means together to resist the forces exerted thereon when the staples are formed.

10. The surgical stapling instrument of claim 9, which includes:

spacer means mounted on one of said jaw members for maintaining a predetermined gap between said staple cartridge and said anvil.

11. The surgical stapling instrument of claim 9, wherein:

at least one of said jaw members is flexible to permit its rear portion to bend away from the rear portion of said other jaw member and its front portion to bend toward the front portion of said other jaw member to urge said staple cartridge and said anvil together.

12. The surgical stapling instrument of claim 9, wherein said cam means comprises:

a cam member pivotally mounted on one of said jaw members at a position remote from said latching means, said cam member being pivotable from a first inoperative position to a second operative position to move said rear portions of said jaw members apart and to urge said front portions of said jaw members together.

13. The surgical stapling instrument of claim 12, wherein:

said cam member includes a first lower cam surface for engaging said other jaw member with said cam member disposed in its first inoperative position and a second higher cam surface for engaging said other jaw member with said cam member disposed in its second operative position.

14. The surgical stapling instrument of claim 13, wherein:

said cam member is operable by said pusher means to move from its inoperative position to its operative postion when said pusher means is advanced.

15. The surgical stapling instrument of claim 14, wherein:

said cam member is operable by said pusher means to return from its operative position to its inoperative postion when said pusher means is retracted.

16. The surgical stapling instrument of claim 12, wherein said pusher bar and knife assembly includes:

a pusher block slidably mounted for longitudinal movement along one of said jaw members and provided with a pair of staple pusher bars adapted to slide into said staple cartridge to sequentially drive said staples into the tissue gripped between said jaw members, and a knife block slidably mounted for longitudinal movement along one of said jaw members and provided with a knife blade adapted to slide into said staple cartridge between said staple pusher bars.

17. The surgical stapling instrument of claim 16, wherein:

said cam member is operable by said pusher block prior to the formation of said staples to urge said staple cartridge and said anvil together.

18. The surgical stapling instrument of claim 17, which includes:

actuator means for initially advancing said pusher block toward said staple cartridge while said knife block remains stationary to actuate said cam member and to initially move said pusher bars into said staple cartridge and for subsequently advancing said knife block toward said staple cartridge upon engagement by said pusher block to move said pusher bars and said knife blade simultaneously into said staple cartridge.

19. The surgical stapling instrument of claim 18, wherein:

said knife block is adapted to slidably receive said pusher bars to permit said pusher block to initially slide relative to said knife block when said pusher block is advanced and retracted.

20. The surgical stapling instrument of claim 19, wherein:

said pusher bars are adapted to engage said knife block as said pusher block is retracted to withdraw said knife blade from said staple cartridge.

21. A surgical stapling instrument, comprising:

first and second cooperating elongate jaw members, one of said jaw members including staple carrying means adapted to receive a plurality of staples arranged in at least one row, and said other jaw member including anvil means adapted to form said staples, pusher means for driving the staples from said staple carrying means into tissue gripped between said jaw members and forming the staples against said anvil means to produce at least one row of staples in the tissue, means for latching said jaw members together with the tissue located between said staple carrying means and said anvil means, and cam means operable after said jaw members are latched together for urging said jaw members apart at a position remote from said latching means to urge said staple carrying means and said anvil means together during the formation of said staples.

22. A surgical stapling instrument, comprising:

first and second cooperating elongate jaw members, one of said jaw members including a staple cartridge mounted at a front portion of said jaw member and adapted to receive at least two laterally spaced longitudinal rows of staples, and said other jaw member including an anvil mounted at a front portion of said jaw member and adapted to form said staples, a pusher bar and knife assembly slidable longitudinally relative to said elongate jaw members, said assembly including pusher means for driving the staples from said staple cartridge into tissue gripped between said jaw members and forming the staples against said anvil to produce a pair of laterally spaced staple rows in the tissue, and knife means for cutting the tissue gripped between said jaw members along a line between said staple rows, means for latching said jaw members together with the tissue located between said staple cartridge and said anvil, and cam means operable after said jaw members are latched together for urging the rear portions of said jaw members apart at a position remote from said latching means to urge said front portions of said jaw members together to clamp said staple cartridge and said anvil against the tissue during the formation of said staples.

* * * * *